US00PP14892P2

(12) United States Plant Patent
Verduin

(10) Patent No.: US PP14,892 P2
(45) Date of Patent: Jun. 8, 2004

(54) ASTILBE PLANT NAMED 'JUMP AND JIVE'

(50) Latin Name: *Astilbe hybrida*
Varietal Denomination: Jump and Jive

(75) Inventor: Harry G. J. Verduin, Heemskerk (NL)

(73) Assignee: Inspiration Plant cv, Lisse (NL)

( * ) Notice: Subject to any disclaimer, the term of this patent is extended or adjusted under 35 U.S.C. 154(b) by 0 days.

(21) Appl. No.: 10/628,757

(22) Filed: Jul. 28, 2003

(51) Int. Cl.[7] ..... A01H 5/00
(52) U.S. Cl. ..... Plt./263
(58) Field of Search ..... Plt./226, 263

*Primary Examiner*—Anne Marie Grunberg
*Assistant Examiner*—Susan B. McCormick-Ewoldt
(74) *Attorney, Agent, or Firm*—C. A. Whealy

(57) ABSTRACT

A new and distinct cultivar of Astilbe plant named 'Jump and Jive', characterized by its upright, mounded and compact plant habit; rapid growth rate; freely and uniform flowering habit; and light red purple-colored flowers.

1 Drawing Sheet

Botanical classification/cultivar designation: *Astilbe hybrida* cultivar Jump and Jive

BACKGROUND OF THE INVENTION

The present Invention relates to a new and distinct cultivar of Astilbe plant, botanically known as *Astilbe hybrida*, and hereinafter referred to by the name 'Jump and Jive'.

The new Astilbe is a product of a planned breeding program conducted by the Inventor in Heemskerk, The Netherlands. The objective of the breeding program is to develop new compact and fast-growing Astilbe cultivars.

The new Astilbe originated from a pollination made by the Inventor of two unidentified *Astilbe hybrida* selections, not patented. The new Astilbe was discovered and selected as a single flowering plant by the Inventor in a controlled environment in Heemskerk, The Netherlands in 1995 from the resultant progeny of the pollination. The new Astilbe was selected on the basis of its rapid growth rate and light red purple-colored flowers.

Asexual reproduction of the new cultivar by divisions taken at Heemskerk, The Netherlands, has shown that the unique features of this new Astilbe are stable and reproduced true to type in successive generations.

SUMMARY OF THE INVENTION

Plants of the cultivar Jump and Jive have not been observed under all possible environmental conditions. The phenotype may vary somewhat with variations in environment such as temperature and light intensity without, however, any variance in genotype.

The following traits have been repeatedly observed and are determined to be the unique characteristics of 'Jump and Jive'. These characteristics in combination distinguish 'Jump and Jive' as a new and distinct Astilbe cultivar:

1. Upright, mounded and compact plant habit.
2. Rapid growth rate.
3. Freely and uniform flowering habit.
4. Light red purple-colored flowers.

Plants of the new Astilbe are most similar to plants of the parent selections. Plants of the new Astilbe differ from plants of the parent selections and other Astilbe cultivars known to the Inventor in leaflet shape and flower color.

BRIEF DESCRIPTION OF THE PHOTOGRAPHS

The accompanying colored photographs illustrate the overall appearance of the new cultivar, slowing the colors as true as it is reasonably possible to obtain in colored reproductions of this type. Colors in the photographs may differ slightly from the color values cited in the detailed botanical description which accurately describe the actual colors of the new Astilbe.

The photograph at the top of the sheet comprises a side perspective view of a typical flowering plant of 'Jump and Jive' grown in a container.

The photograph at the bottom of the sheet is a close-up view of a typical inflorescence and leaves of 'Jump and Jive'.

DETAILED BOTANICAL DESCRIPTION

Plants shown in the aforementioned photographs and used in the following description were grown in containers under conditions which closely approximate commercial production conditions during the spring and summer in an outdoor nursery in Heemskerk, The Netherlands. Plants in the photographs and those used for the description were about one year old when the photographs and description were taken. In the following description, color references are made to The Royal Horticultural Society Colour Chart, 1995 Edition, except where general terms of ordinary dictionary significance are used.

Botanical classification: *Astilbe hybrida* cultivar Jump and Jive.

Parentage:

*Female, or seed, parent.*—Unidentified *Astilbe hybrida* selection, not patented.

*Male, or pollen, parent.*—Unidentified *Astilbe hybrida* selection, not patented.

Propagation:

*Type.*—By divisions.

*Time to rooting.*—About one month at 18° C.

*Root description.*—Fine.

Plant description:

*Form.*—Perennial. Upright, mounded and compact plant habit; inverted triangle. Flowering stems and leaves arise from the roots; dense and bushy plant habit; moderately vigorous growth habit. Freely flowering with numerous flowers on numerous branched panicles.

*Growth rate.*—Rapid; from divisions, about 20 weeks are required to produce fully-grown flowering plants in 17-cm containers.

*Plant height.*—About 40 cm.

*Plant width.*—About 45 cm.

*Stem description.*—Length: About 36 cm. Internode length: About 8 cm. Texture: Sparsely pubescent. Color: 144B.

*Foliage description.*—Arrangement: Alternate; bi-ternately compound. Leaf length (including petiole): About 35 cm. Leaf width: About 20 cm. Leaflet length: About 8 cm. Leaflet width: About 3.5 cm. Leaflet shape: Ovate to elliptic. Leaflet apex: Acuminate to acute. Leaflet base: Cuneate to oblique. Leaflet margin: Serrate, occasionally doubly serrate. Leaflet texture, upper and lower surfaces: Sparsely pubescent. Leaflet venation pattern: Pinnate. Leaflet color: Developing and fully expanded foliage, upper surface: 144A; venation, 145C, Developing and fully expanded foliage, lower surface: 143C; venation, 145D. Petiole length: About 15 cm. Petiole diameter: About 2.5 mm. Petiole texture, upper and lower surfaces: Smooth, glabrous. Petiole color, upper and lower surfaces: 144B.

Flower description:

*Flower arrangement and shape.*—Numerous single flowers arranged in branched panicles; flowers face mostly outwardly. Freely and uniformly flowering habit; about 1,000 flowers and flower buds per plant.

*Natural flowering season.*—Continuous flowering during the early summer in The Netherlands.

*Flower longevity on the plant.*—Individual flowers last about three weeks on the plant and about one week as a cut flower. Flowers persistent.

*Fragrance.*—Faint musty odor, not unpleasant.

*Flower buds.*—Length: About 1.5 mm. Diameter: About 1.5 mm. Shape: Ovate to orbicular. Color: 68B.

*Flowers.*—Diameter: About 3 mm. Depth (height): About 2 mm.

*Petals.*—Quantity per flower: Five. Length: About 3.5 mm. Width: About 2 mm. Shape: Ligulate to linear. Apex: Obtuse. Margin: Entire. Texture, upper and lower surfaces: Smooth, glabrous. Color: When opening and fully opened, upper surface: 68B. When opening and fully opened, lower surface: 68B.

*Sepals.*—Quantity per flower: Five. Calyx length: About 5 mm. Calyx width: About 6 mm. Shape: Ovate. Apex: Obtuse. Margin: Entire. Texture, upper and lower surfaces: Smooth, glabrous. Color, upper and lower surfaces: 65D.

*Pedicles.*—Length: About 1 mm. Diameter: Less than 1 mm. Color: 37A.

*Reproductive organs.*—Stamens: Quantity per flower: About ten. Anther attachment: Basifixed. Anther length: Less than 0.5 mm. Anther color: Creamy white to light gray. Pollen amount: Sparse. Pollen color: 19A. Pistils: Quantity per flower: Two. Pistil length: About 2 mm. Stigma shape: Club-shaped. Stigma color: Close to 19C. Style length: About 1.5 mm. Style color: Close to 66D. Ovary color: Close to 66D.

*Seed.*—Length: Less than 0.5 mm. Diameter: Less than 0.5 mm. Color: Light brown.

Disease/pest resistance: Plants of the new Astilbe have not been noted to be resistant to pathogens and pests common to Astilbe.

It is claimed:

1. A new and distinct cultivar of Astilbe plant named 'Jump and Jive', as illustrated and described.

* * * * *

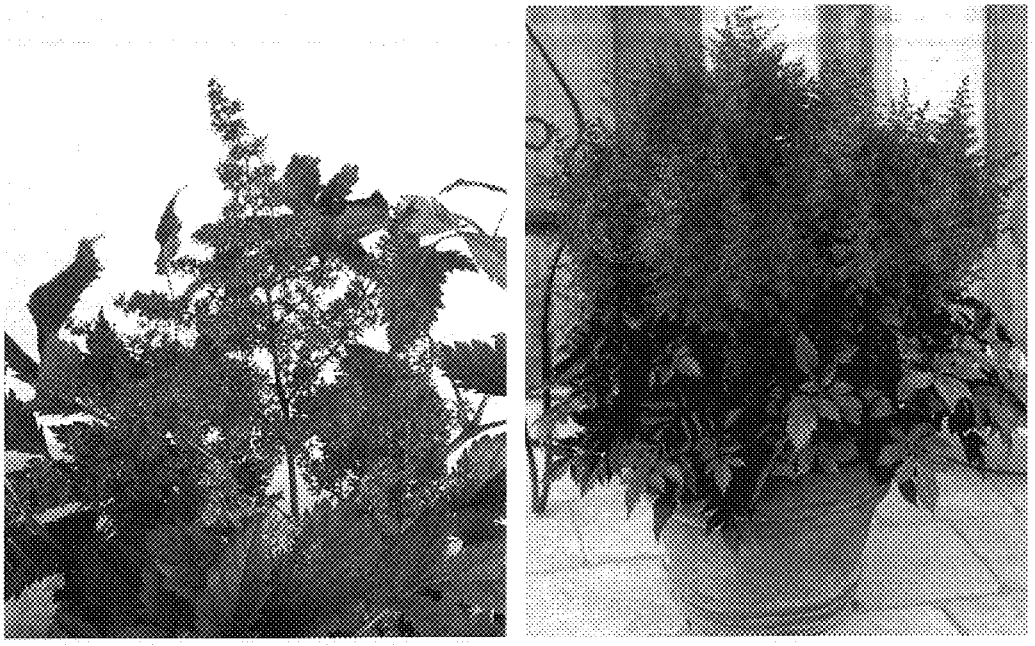
Jump and Jive